United States Patent [19]
Zibell

[11] Patent Number: 4,523,595
[45] Date of Patent: Jun. 18, 1985

[54] METHOD AND APPARATUS FOR AUTOMATIC DETECTION AND TREATMENT OF VENTRICULAR FIBRILLATION

[76] Inventor: J. Scott Zibell, 40 Brittany Ct., Charlotte, N.C. 28226

[21] Appl. No.: 325,061

[22] Filed: Nov. 25, 1981

[51] Int. Cl.³ .............................................. A61N 1/36
[52] U.S. Cl. ............................................. 128/419 D
[58] Field of Search ..................... 128/419 D, 702–705

[56] References Cited

U.S. PATENT DOCUMENTS

| Re. 30,372 | 8/1980 | Mirowski et al. | 128/419 D |
| 3,554,187 | 1/1971 | Glassner | 128/703 |
| 3,616,790 | 11/1971 | Harris | 128/702 |
| 3,805,795 | 4/1974 | Denniston et al. | 128/419 D |
| 3,807,392 | 4/1974 | Harris | 128/702 |
| 4,088,138 | 5/1978 | Diack et al. | 128/419 D |
| 4,202,340 | 5/1980 | Langer et al. | 128/419 D |
| 4,275,742 | 6/1981 | Faisandier | 128/704 |
| 4,291,699 | 9/1981 | Geddes et al. | 128/419 D |
| 4,295,474 | 10/1981 | Fischell | 128/419 D |
| 4,303,075 | 12/1981 | Heilman | 128/419 D |
| 4,316,249 | 2/1982 | Gallant et al. | 128/702 |
| 4,336,810 | 6/1982 | Anderson et al. | 128/702 |
| 4,432,375 | 2/1984 | Angel et al. | 128/419 D |

FOREIGN PATENT DOCUMENTS 2000682 1/1979 United Kingdom ........... 128/419 D

Primary Examiner—William E. Kamm
Assistant Examiner—Mitchell J. Shein
Attorney, Agent, or Firm—Jim Zegeer

[57] ABSTRACT

Ventricular fibrillation (VF) is detected by comparing the electrocardiogram (ECG) waveform of the patient's heart against a stored library of compilation of waveform characteristics of various heart conditions as recorded by an ECG. Since the waveform for ventricular fibrillation of arrythmias are completely unformed compexes, disorganized and irregular, the presence or absence of any of the stored or library features in the patient ECG is used as the criteria for diagnosing VF and automatically subjecting the patient to a prescribed electroshock therapy.

13 Claims, 46 Drawing Figures

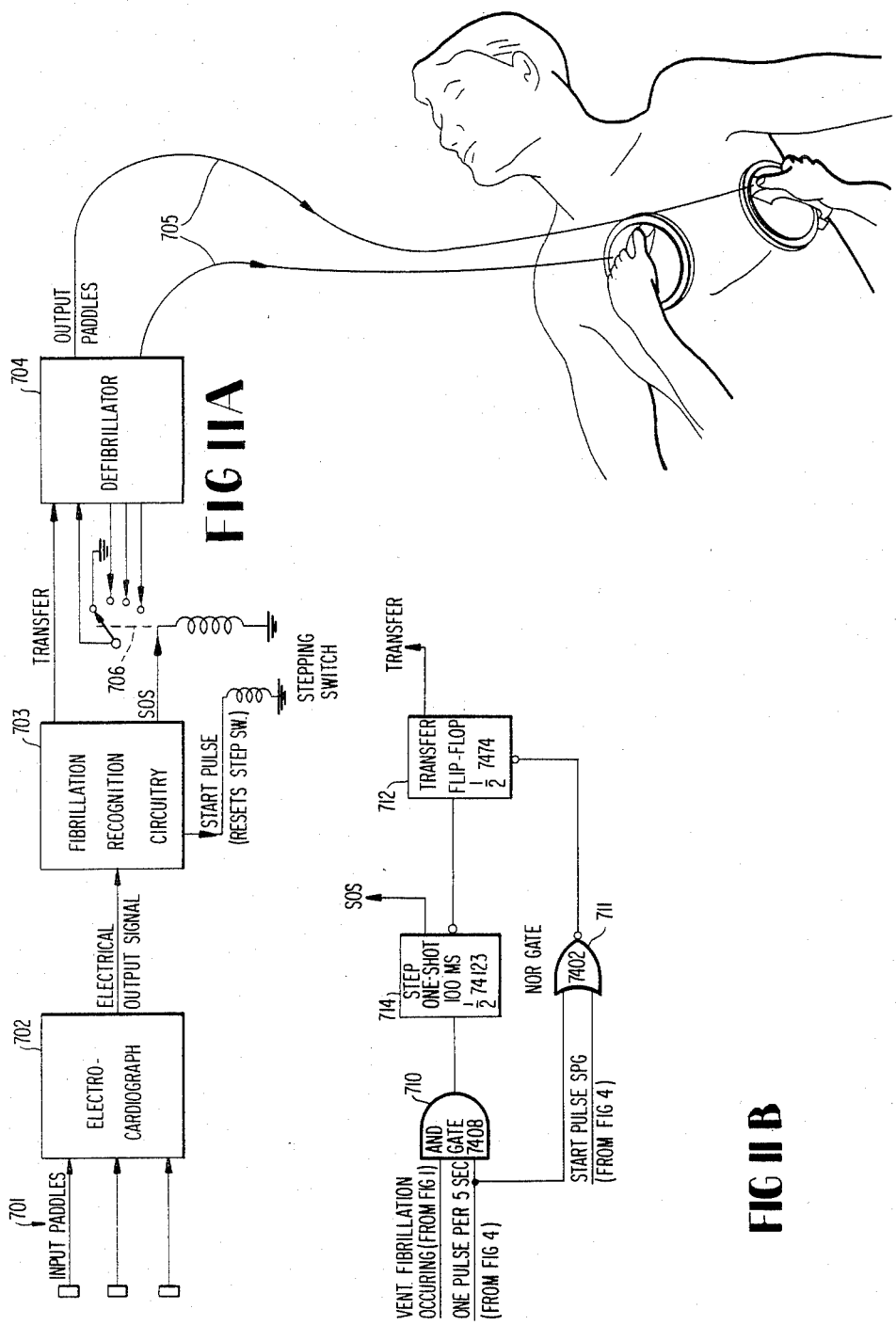

E 23 THE DYING HEART - VENTRICULAR FIBRILLATION
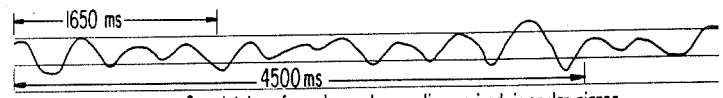
Completely unformed complexes - disorganized irregular zigzag SINUS RHYTHMS (normal P wave preceding every QRS)
E 1
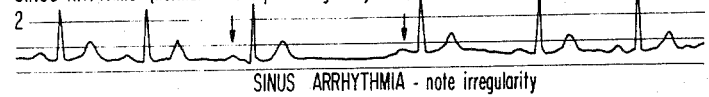
SINUS ARRHYTHMIA - note irregularity

E 2
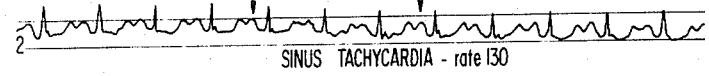
SINUS TACHYCARDIA - rate 130

E 3
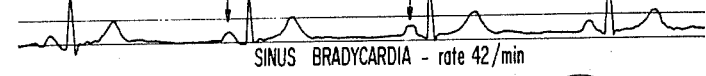
SINUS BRADYCARDIA - rate 42/min

ATRIAL PREMATURE BEAT
E 4
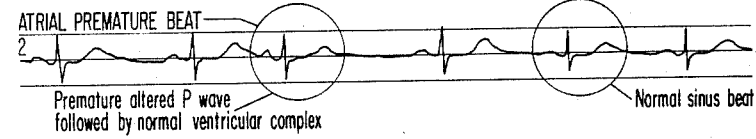
Premature altered P wave followed by normal ventricular complex — Normal sinus beat

E 5
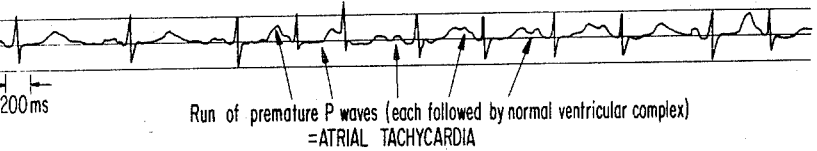
200ms
Run of premature P waves (each followed by normal ventricular complex) = ATRIAL TACHYCARDIA 2 examples of ATRIAL TACHYCARDIA: in each the QRS is normally narrow
E 6
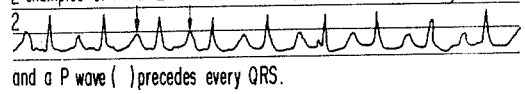
and a P wave ( ) precedes every QRS.

E 7

ATRIAL TACHYCARDIA WITH 2 to 1 A-V BLOCK
E 8
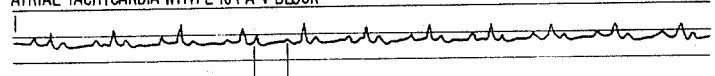
Two P waves for every QRS - only every alternate impulse is conducted to the ventricles.
"Sawtooth" atrial flutter ("FF") waves in regular relationship to QRS.

E 9
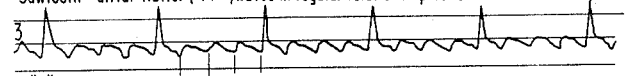
4 "F" waves to each QRS = 4 to 1 A-V conduction.
When the A-V ratio is 2 to 1 (as it most often is) the F waves are not always easy to spot(↑)

E 10
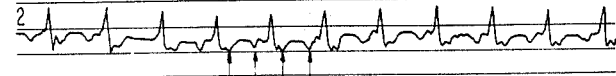

E 11
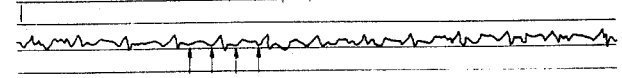

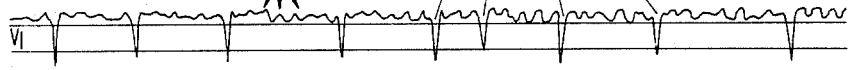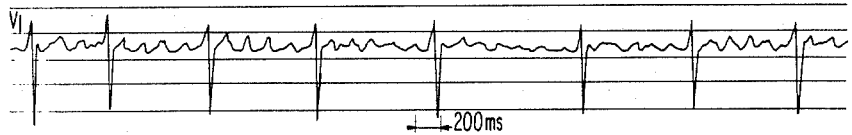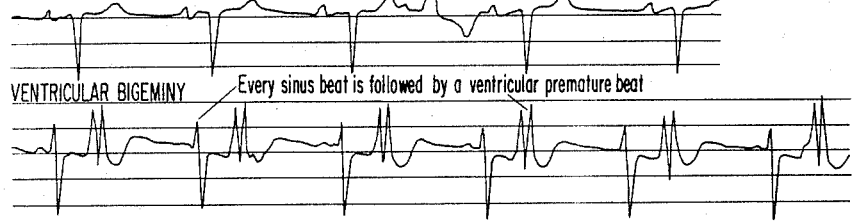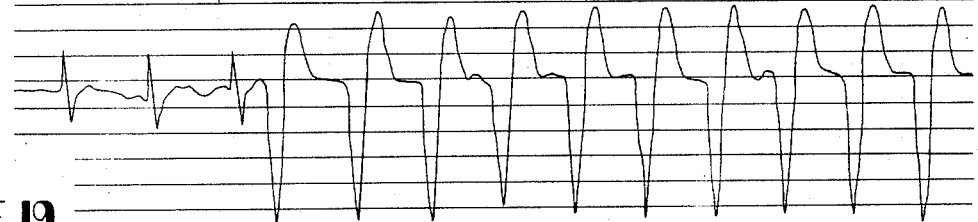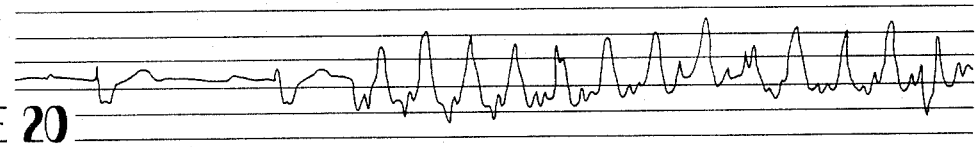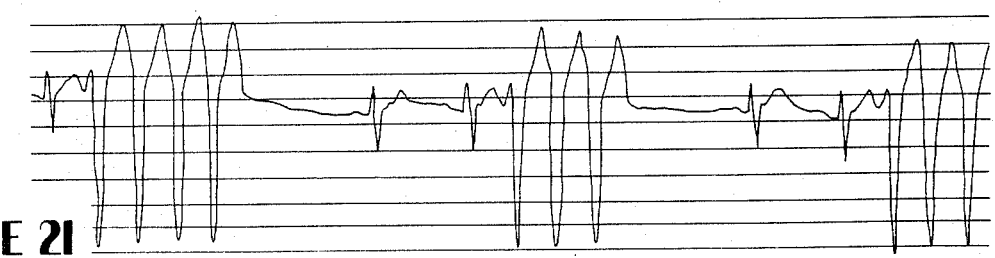

Two examples of VENTRICULAR TACHYCARDIA
Independent P waves
(i.e., changing P to QRS relationship)

E 17

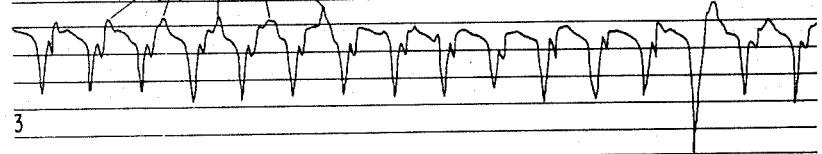

E 18

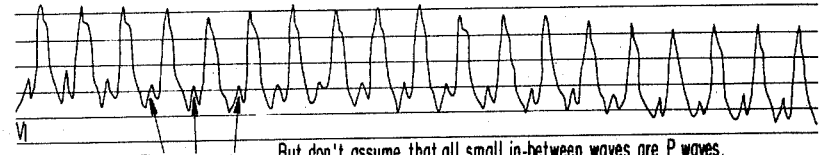

These are not. But don't assume that all small in-between waves are P waves. If they move along independently, as they do in FIG E 17, you know they're P waves. If they don't you often can't be sure.

THE DYING HEART-
VENTRICULAR FLUTTER —————Semi-formed complexes-regular zigzag—————

E 22

TWO EXAMPLES OF
A-V NODAL RHYTHM

E 24

E 25

Abnormal P waves(↓) either shortly before of after QRS.

1ST DEGREE A-V BLOCK ——— P-R interval prolonged

E 26

2ND DEGREE A-V BLOCK

E 27

——— P-R intervals progressively lengthen until a beat is blocked (↓)-Wenckebach phenomenon HIGH GRADE (3 TO 1) A-V BLOCK becoming complete A-V block in the lower strip        (strips are continuous)
3 Ps to each QRS

E 28

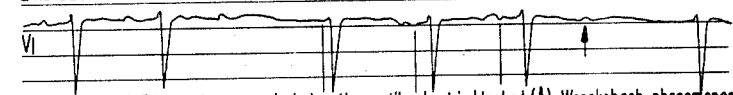

E 29 ventricular standstill

HIGH GRADE (2 to 1) A-V BLOCK

E 30

———— 2 waves to each QRS ————

COMPLETE A-V BLOCK

E 31

Changing P to QRS relationship - Ventricles slow and regular - idioventricular rhythm

METHOD AND APPARATUS FOR AUTOMATIC DETECTION AND TREATMENT OF VENTRICULAR FIBRILLATION

BACKGROUND AND BRIEF DESCRIPTION OF THE INVENTION

Statistics reveal that in excess of three thousand persons suffer heat attacks each day. Over one thousand of these die. It has been clinically proved the quicker the right aid can be administered to the victim the better the chances for recovery. Of the one thousand plus who die each day, over one half could be saved by receiving effective treatment quickly enough to offset the damage done in the early stages of the attack. Also, of the two thousand or so who "survive", the severity of the damage, or impairment, could be reduced substantially by receiving effective treatment quickly enough. The immediate effect of an acute myocardial infarction which leads to fatality is ventricular fibrillation or VF. Ventricular fibrillation is amenable to treatment by electroshock via a defibrillator, and this treatment is currently employed in hospital emergency areas and coronary care units, as well as by some emergency rescue units.

The complexities of operating this equipment, which, in some cases, requires interpretation of oscilloscope displays and the like greatly limit its use. In addition, the high cost of presently available equipment puts it beyond the financial reach of many in these groups. Consequently, many of the one million plus "heart" victims each year are outside the area of the quality assistance they need within the critical time they need it.

This number one killer and crippler of modern man effects those our society can least afford to lose. Too many of our leaders and/or executors in the religious, cultural, academic, professional, business, financial, and political areanas are struck down in their prime. The survivors, are severally penalized through the loss of their talents and possible contributions by their untimely demise.

The object of this invention is to provide self-monitoring, self-evaluating machines in great enough availability so that these victims can receive quality assistance within the critical framework of time to prevent either death or debilitating after effects.

The electrocardiogram waveform for a heart in the arrhythmic condition of ventricular fibrillation is unique in that it consists of completely unformed complexes-disorganized-irregular. In contrast, practically all the others have certain repetitive characteristics even though they may contain irregularities. From this, this invention is based on the fact that certain wave components will maintain a rather consistant amplitude; both those above the line-the P, R and T curves-and those below, the Q and S. Even when the pulse rate varies, a pattern repeat is discernible, sometimes after several pulse beats. According to this invention, the wave is sampled, analyzed for peaking repetitively within a preset amplitude variance, check these peaks in a selected time frame, compare the slope of a segment- say either the Q-R or the R-S in several beats over a monitoring period of some five to ten or so seconds to distinguish many similarities in all conditions except in ventricular fibrillation. Should at least a minimal number of similarities be detected in this period, it can quite safely be assumed the heart is not in ventricular fibrillation. Whereas in the case of mismatch where similarities might occur at random and then only in few instances, it could quite safely be assumed the heart is in ventricular fibrillation VF. This condition would activate the machine. The exception to this would be where the amplitude is minimal-ventricular standstill. In the "flat-line" condition, an external pacer should take control to reestablish the pulse beat. The more severe shock as induced for ventricular fibrillation would not correct this condition.

The automatic defibrillator according to this invention includes conventional electrode or paddle means for application to a patient's chest, means for storing a plurality of known electrocardiogram waveform characteristics of various heart conditions, the electrodes are coupled to conventional ECG circuitry for producing an electrocardiogram waveform of the patient's heart and an electrical circuit is provided for comparing the electrocardiogram waveform of said patient against each stored characteristic.

A determination is made of the presence or absence of all stored electrocardiogram waveform characteristics of various heart conditions in the electrocardiogram of said patient and a defibrillator is activated to apply defibrillating electrical energy to said patient via the electrodes upon detecting the absence of all stored electrocardiogram waveform characteristics of various heart conditions in said patient's electrocardiogram.

BRIEF DESCRIPTION OF THE DRAWINGS

The above and other objects, advantages and features of the invention will become more apparent when considered with the following specification and accompanying drawings wherein:

FIG. 11a illustrates the block diagram of the automatic defibrillation apparatus of this invention and FIG. 11b shows in greater detail the control circuitry for operating the defibrillation unit shown in FIG. 11a, and FIGS. E1-E31 are electrocardiogram waveforms which are used to illustrate and explain multiplicity of characteristics and features of heart conditions reflected in electrocardiograms, FIG. 23 illustrating the dying heart and exemplifying ventricular fibrillation.

There are three major characteristics of the electrocardiogram (ECG) waveform whose presence, separately or together, indicate that Ventricular Fibrillation is not occurring. These are:

(1) Peak voltages which are large compared to the average voltage.

(2) Peak slopes (dV/dt) which are large compared to average slopes.

(3) Waveforms having a faily uniform period of repetition.

Ventricular Fibrillation, on the other hand, exhibits an almost completely random, non-repetitive pattern showing no sharp peaks.

The object of the present invention and the circuits shown herein is to detect the presence or absence of various combinations of these waveform characteristics; if none of them are present to any significant degree, the heart is assumed to be in a state of fibrillation. Some exceptions occur; provisions for dealing with these are included in the circuitry and will be discussed herein after.

DISCUSSION OF THE OVERALL BLOCK DIAGRAM OF FIG. 1

Figure 1:
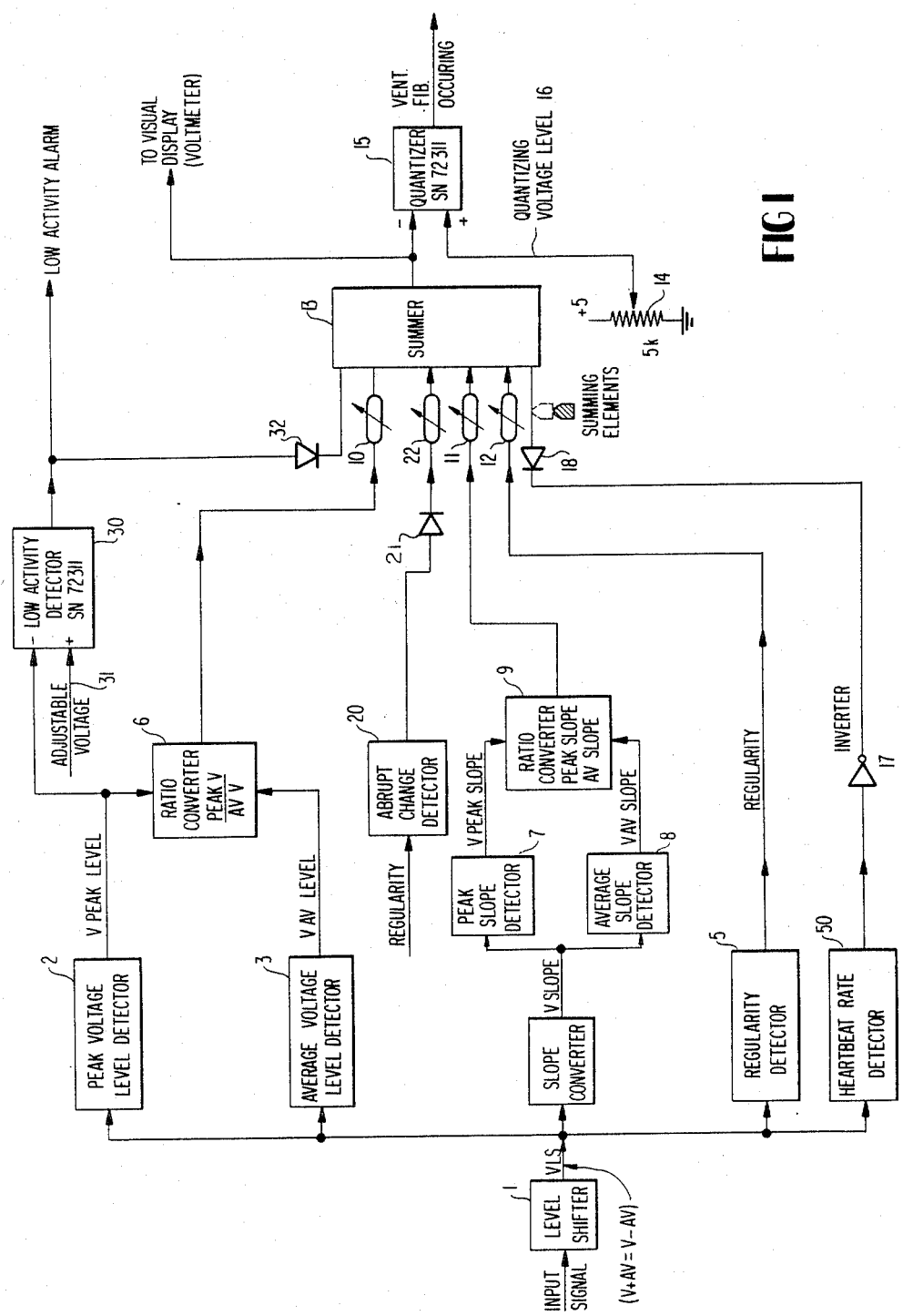
FIG. 1 is a block diagram of a fibrillation detector incorporating the invention.

FIG. 1 shows an overall block diagram of the fibrillation detector. The input signal from the ECG equipment (which can have any of the waveforms shown in the anatomy of ECG waveforms of FIGS. E1 to E31, inclusive) drives level shifter 1, producing waveforms $V_{LS}$. Level Shifter 1 converts a signal which has an unknown DC base line shift into a signal which has a voltage level whose average voltage above ground is equal to the average voltage below ground.

This signal, $V_{LS}$, is used to drive a number of circuits which will analyze the waveform for characteristics which are significant.

As shown in FIG. 1, the first of these circuits is the peak voltage level detector 2, which produces an output which is approximately equal to the largest voltage excursion during the selected time period, say past ten seconds. This may be either a positive or negative peak. The second of these circuits is the average voltage level detector 3, which produces a voltage approximately equal to the average positive voltage above ground during the last ten seconds or selected time period. This is equal, because of level shifter 1, to the average negative voltage.

Since the input ECG signal varies in amplitude a great deal from situation to situation, it is important to normalize these measurements by deriving the ratio of the peak voltage level to the average voltage level. This is done by ratio converter 6.

The third of these circuits, is slope converter 4, which converts the $V_{LS}$ waveform into a signal which is proportional to the time-rate-of-change of $V_{LS}$. This signal is a voltage whose value at any instant is proportional to the slope of $V_{LS}$.

Peak slope detector 7 produces an output which is approximately equal to the largest slope during the last ten seconds. This may be either a positive or a negative slope.

Average slope detector 8 produces an output which is approximately equal to the average slope during the last ten seconds.

In order to obtain a measurement which is as free as possible from perturbations caused by variations in the input signal amplitude, the ratio of the peak slope to the average slope is derived by ratio converter 9.

The regularity (or periodicity) of the ECG waveform is also important to measure. This is done in the regularity detector 5.

The outputs of these three most important measuring circuits, peak V/Av V, peak slope/Av slope, and regularity, are added together in the summer 13, via the adjustable summing elements 10, 11 and 12. The values of these summing elements can be obtained by experimental operation of the equipment; it is expected that they will remain fixed during the normal operating life of the equipment. Three other signals, produced by the low activity detector 30, the abrupt change detector 20, and the heartbeat rate detector 50 are additional inputs to the summer, as will be explained later herein.

The output of summer 13 is presented to one input of quantizer 15. The object of this quantizer 15 is to make a GO/NO GO decision as to whether to apply defibrillating electrical stimulus to the patient. Note that the larger the output of the summer, the less likely it is that a fibrillation condition exists. The summer output, then, is presented to the negative input of quantizer 15, while a quantizing voltage level is applied to the positive input of the quantizer. The quantizing voltage level is derived from potentiometer 14, set at the factory, and normally fixed during the life of the equipment.

If the summer output is more negative than the quantizing voltage level, the quantizer puts out a positive voltage level indicative of ventricular fibrillation occuring and this output line activates the electrical stimulus.

OPERATION OF THE EQUIPMENT USING SPECIFIC INPUT WAVEFORM EXAMPLES

Specific input waveform examples are shown in FIGS. E1 through E31. These examples are taken from an instruction manual used to train cardiologists, and are representative of many different forms of heart disease whose characteristics and/or features appear in the electrocardiogram. If desired, the invention could be used to detect any of these waveforms.

The following paragraphs discuss how the equipment shown in FIG. 1 will analyze each of these waveform classes to detect the occurrence of the fibrillation condition.

FIG. E1 shows an example of sinus arrythmia. The peak V/Av V circuits will produce a high voltage as will also the peak slope Av slope. The regularity detector will not produce a high voltage, but the sum will be sufficiently high to indicate a non-fibrillation condition.

FIG. E2 shows an example of sinus tachcardia. The peak V/Av V will not produce as high a voltage in this example as in the previous example; the peak slope Av slope will produce a high voltage, however, and the regularity output will be high.

FIG. E3 shows an example of sinus bradycardia. The waveforms here are similar to E1, except that the regularity is better.

E4 shows an atrial premature beat. The waveforms as far as the invention is concerned are similar to example E1, showing good level and slope ratios, but poor regularity.

E5, an example of atrial tachycardia, will have good output from the slope ratio circuit 9, but will produce low outputs from the level ratio converter circuit 6 and regularity circuits 5.

FIGS. E6 and E7 are further examples of atrial tachycardia, but both produce good outputs from all three measuring circuits.

FIG. E8 is the ECG waveform from an atrial tachycardia condition with 2 to 1 A-V block. Although the overall amplitude of the input signal is small, the measurement circuits will give good outputs, since the signals have been normalized.

FIGS. E9, E10 and E11, exemplifying atrial flutter, will all produce good output signals; preamplification of some waveforms, such as the E11 waveform before presentation to the measuring circuits is conventional.

E12 and E13 (atrial fibrillation) show waveforms in which the apparent R pulse is negative. This is accomodated by the invention, since both positive and negative excursions are measured.

E14 shows a case of ectopic ventricular beats. The QRS complex shows large excursions both positively and negatively, but this will not confuse the ratio converters. The regularity signal will occassionally be low.

E15 is an example of an atrial premature beat; the measurement outputs will be substantially similar to the results from E14.

FIG. E16 (ventricular begeminy) is unusual in that it contains a rather large number of sharp peaks. As will be later shown by actual computation, however, the measurements will correctly classify this as a non-fibrillation pattern.

FIGS. E17 through E21 are examples of ventricular tachycardia. Although the level and slope ratio outputs will be relatively low for E17 and E18, the regularity output will remain high. E19, E20, and E21 however, contain abrupt changes in the patterns which will cause unreliable measurements. This condition will be detected by the abrupt change detector 20 (FIG. 1); it is added into the summer via diode 21. The high output indicates abrupt pattern changes, while the low output indicates the absence of such changes. The diode is used because the high output from this circuit should be weighted very heavily, while the low output does not carry much information. The high output will prevent any automatic decision to produce shock thereapy until after the waveform pattern has settled down (if it ever does).

Example E22 shows a waveform characteristic of ventricular flutter. The outputs of the ratio converters will be low, for this condition, but the regularity will be high. If the heartbeat rate exceeds 200/min, shock treatment will be initiated; this circuit is the heartbeat rate detector 50.

Waveform example E23 is due to ventricular fibrillation, the condition which the equipment is primarily designed to detect. As will be shown by mathematical computation in later paragraphs, the peak V/Av V will be very low, as will the peak slope/Av slope, and the regularity. Thus, the output of summer 13 will be lower than the quantizing voltage level 16, and a signal will be sent from quantizer 15 to activate the shock treatment.

E24 and E25 are examples of A-V nodal rhythm. The ratio outputs and the regularity output will all be high for this case.

1st degree A-V block (E26) will produce high outputs from the three major circuits. 2nd degree A-V block (E27) will show poor regularity, but the ratios will remain high.

Waveforms E28 and E29 are both part of one continuous recording. When ventricular standstill occurs the low activity detector 20 produces a high output, which is introduced to the summer 13 via diode 32. This prevents a false recognition of fibrillation. The output of the low activity detector can also be used to produce an alarm of any desired type. Adjustable voltages 31 produces the threshold level for the low activity detector; it is set by experience.

FIGS. E30 and E31 show waveforms which are handled normally by the ratio and regularity circuits.

CALCULATION OF EXAMPLES

In order to demonstrate the (theoretical and actual) behaviour of the instrument, a graphical analysis has been performed on three of the most significant waveforms. These are shown in FIGS. 5, 6 and 7.

Figure 5A:
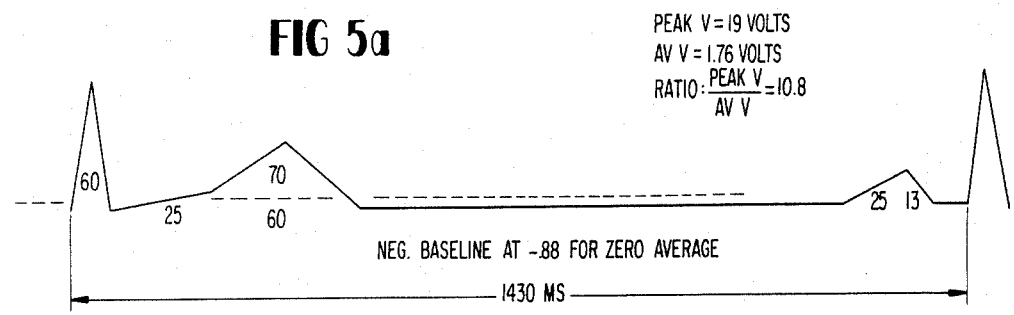
Figure 5B:
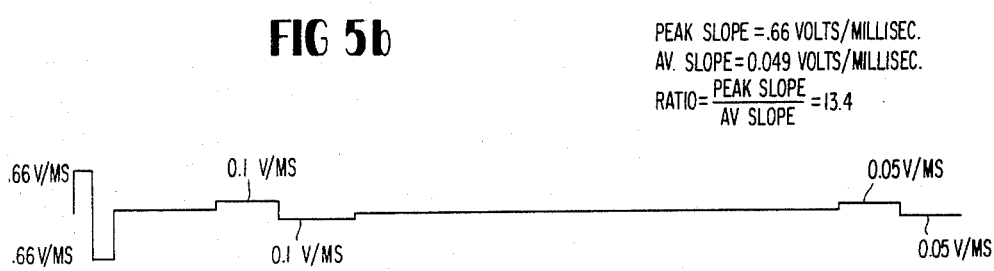

The waveform source for FIG. 5 is the non-fibrillating condition shown in FIG. E3. In order to simplify the calculations, straight line approximations have been used. The upper waveform (FIG. 5a) is the approximation to the voltage waveform of FIG. E3. The voltage axis (vertical) is an arbitrary scale, but the time axis (horizontal) is in the close agreement with the actual sample. The calculation shows that the peak voltage is 19 volts, while the average voltage is 1.76 volts. The peak V/Av V ratio is thus equal to 10.8.

The bottom waveform (FIG. 5b) shows the calculated rates of voltage change for the various parts of the upper waveform. The peak slope is 0.66 volts per millisecond, while the average slope is 0.049 volts per millisecond. Their ratio is 13.4.

Figure 6A:
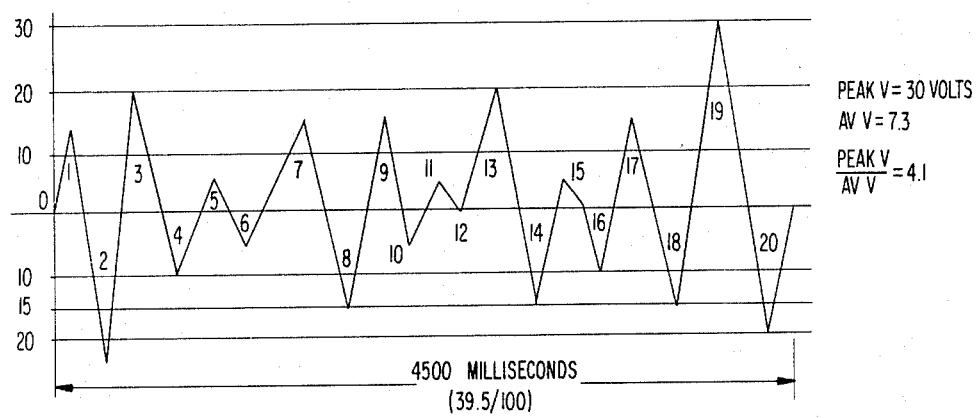
FIG. 6a and FIG. 6b are simplified explanatory waveform diagrams of the fibrillating condition shown in FIG. E-23.
Figure 6B:
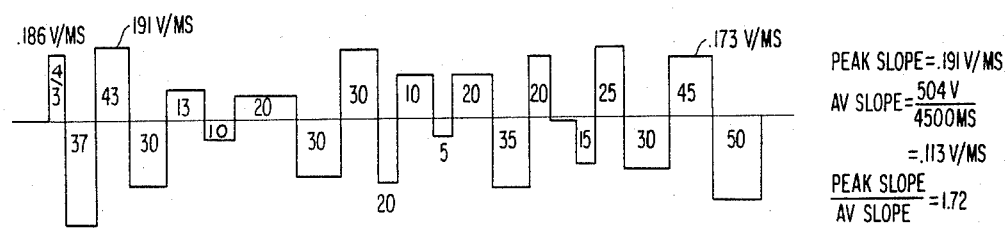
Figure 7A:
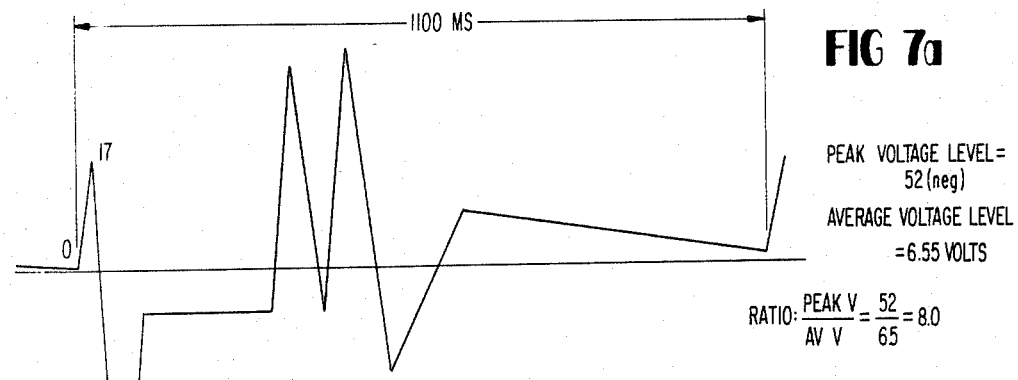
FIG. 7a and FIG. 7b are simplified explanatory waveform diagrams of the non-fibrillating condition shown in FIG. E-16.
Figure 7B:
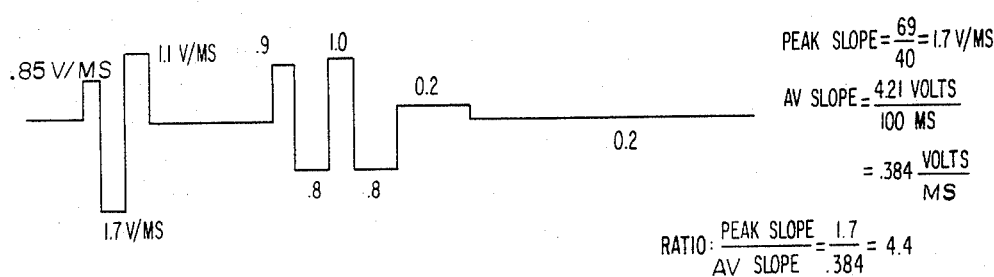

These ratio values from FIG. 5 are to be contrasted with the ratio values derived from FIG. 6. The source waveform for FIG. 6 is that shown in Example E23, which is taken from an ECG of a fibrillating heart. The peak voltage is 30 volts, the average voltage is 7.3 volts, and their ratio is only 4.1. The bottom waveform (FIG. 6b) shows the values of the slopes. The peak slope is 0.191 volts per millisecond, while the average slope is 0.113 volts per millisecond. The ratio is 1.72.

These results show that a non-fibrillating condition produces much higher ratios than the fibrillating condition.

For purposes of further explanation, the non-fibrillating example of E16 is analyzed in FIG. 7. This is an unusual case in that it has four large, sharp spikes for each cycle of the heartbeat, and it is expected that the ratios will be smaller than those of FIG. 5. The calculated peak voltage level is 52, the average voltage level is 6.5, yielding a peak V/Av V ratio of 8. The peak slope is 1.7, with an average slope of 0.384 volts per millisecond, yielding a slope ratio of 4.4. These values are substantially larger than their counterparts derived from the fibrillating waveform and provide a still reasonable degree of distinction.

Figure 4:
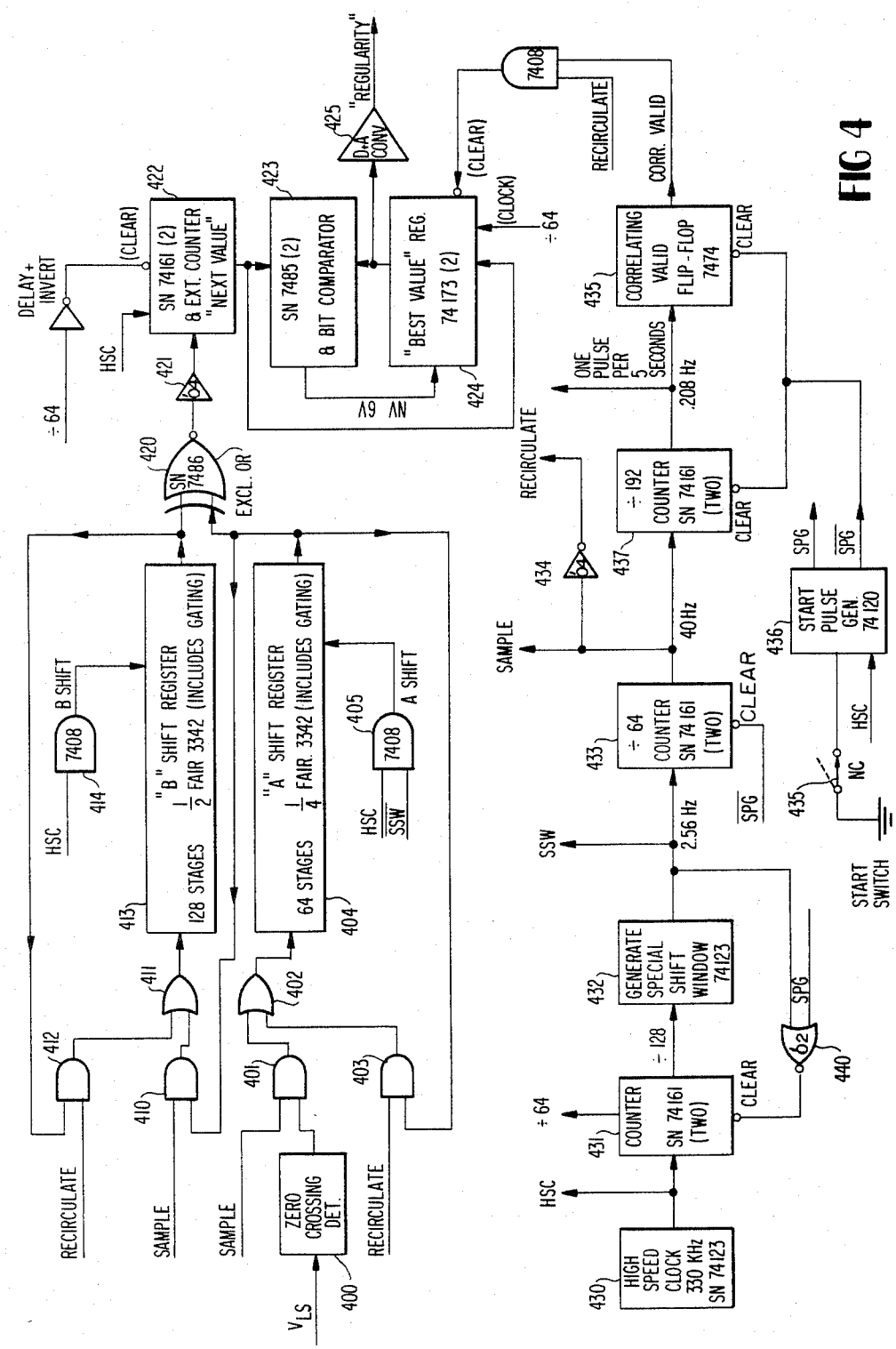
FIG. 4 is a circuit diagram of the regularity detector 5 shown in FIG. 1, FIG. 5a and FIG. 5b are simplified explanatory waveform diagrams of the non-fibrillating condition shown in waveform diagram E-3.

Similar graphical studies for the theroetical output of a regularity detector based on a 4 level version of the circuits shown in FIG. 4 have been made. (This circuit will be discussed in detail in later paragraphs.) These studies show a correlation of greater than 90% within the repetitive patterns of FIGS. E3 and E16 (non-fibrillating) while the best correlation found within the pattern waveform of FIG. E23 was 59% (fibrillating condition).

DETAILED DISCUSSION OF CIRCUITS

Figure 2:
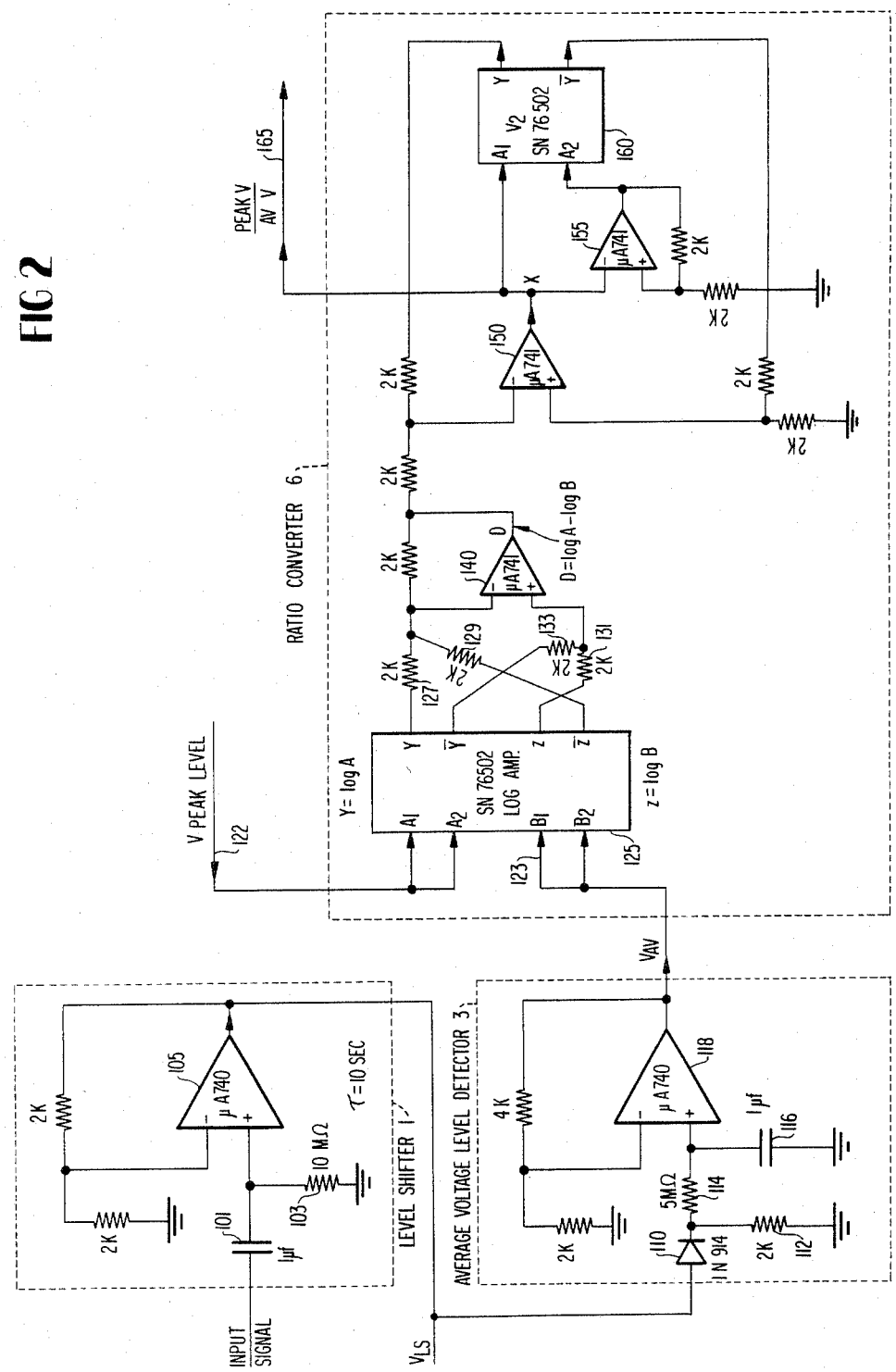
FIG. 2 illustrates a peak voltage detector, average voltage level detector and ratio converter circuits of FIG. 1, FIG. 3 are circuit diagrams of the slope converter 4 average and peak slope detector 7 shown in FIG. 1.

FIG. 2 shows circuitry details of the level shifter 1, the average voltage level detector 3, and the ratio converter 6. The circuitry shown is of the analog type, rather than digital, although both types can be used and even intermixed.

The input signal from the electrocardiogram is brought in first to level shifter 1. The object of this circuit is to produce a waveform which has an average value of voltage above ground equaling the average value below ground. To accomplish this a differentiating circuit is used which has a time constant long in comparison to the maximum period of those signals carrying useful information. This has been chosen to be a ten second time constant, produced by the combination of capacitor 101 and resistor 103. Ths resulting signal is now of high impedance and must be converted again to a low impedance before it can be used to drive other circuits. This is accomplished by using the operational amplifier 105; the operation amplifier used here must have an input impedance very much larger than 10 megohms, and this is done by utilizing a FET input integrated circuit of a type similar to the uA740. Unity voltage gain is satisfactory here, and this is provided by the feedback path using the 2 kilohm resistors. The output of this stage is called $V_{LS}$.

One of the stages $V_{LS}$ drives is the average voltage level detector 3. The object of this stage is to provide an output voltage which is twice the average voltage above ground of the signal $V_{LS}$. To accomplish this the signal is first rectified by diode 110 and resistor 112; it is then integrated over a period of approximately 5 seconds. This integration is provided by the 5 megohm resistor 114 and the 1 uF capacitor 116. The resulting signal must again be reduced in impedance, and this is accomplished by using another high input impedance operational amplifier 118. Because the value of average voltage measured by the integrating circuit is only one half of the total value (the other half consists of signals that are negative with respect to ground) the voltage gain of operational amplifier 118 is set to be a factor of two; this is accomplished by using values of 4 k and 2 k in the feedback path.

Figure 3:
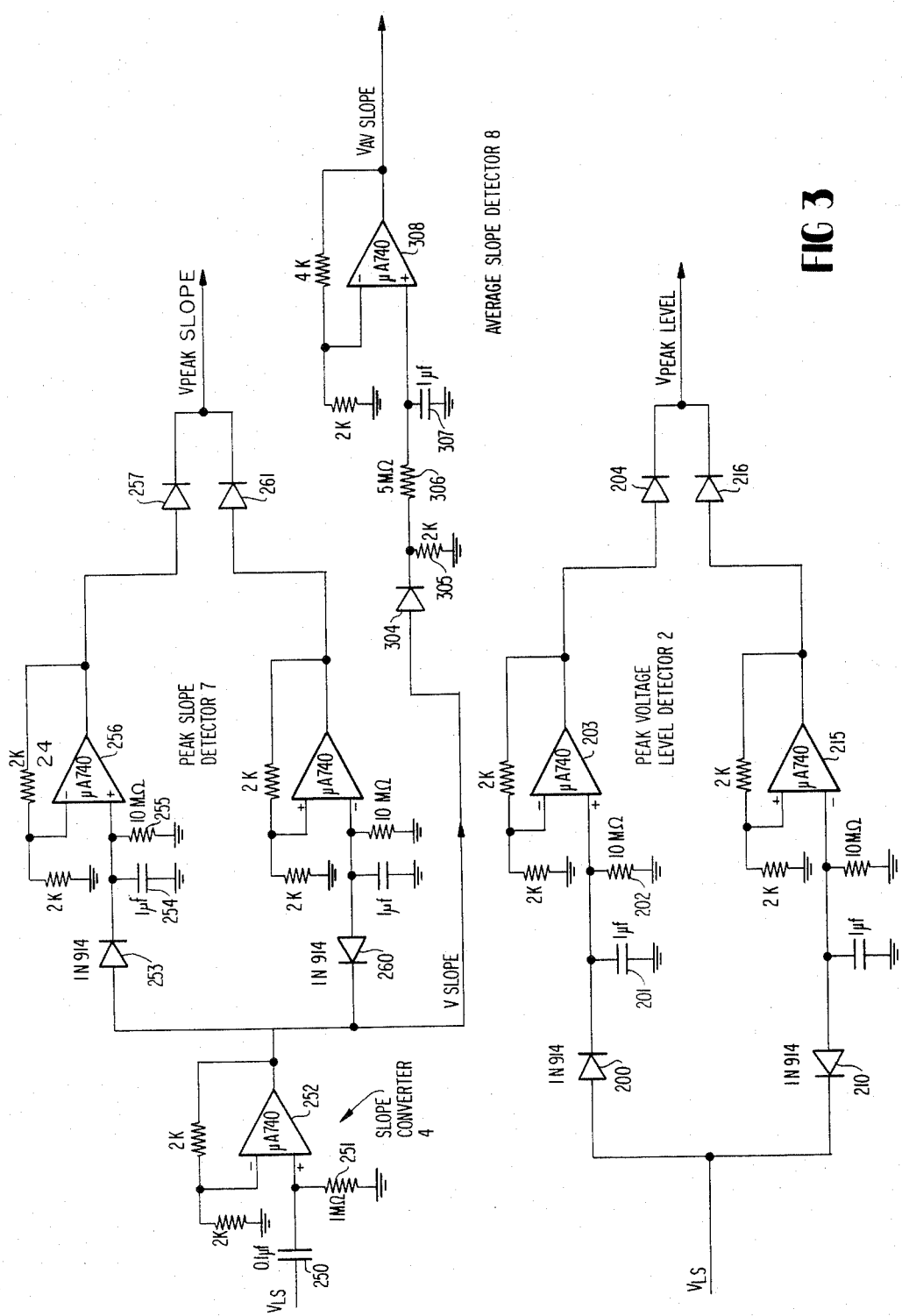

Signal $V_{LS}$ also drives a circuit which produces a voltage proportional to the largest peak of the waveform. This circuit is shown in FIG. 3. It consists of a positive section and a negative section, since the peak voltage may be either positive or negative with respect to ground. In the positive section, $V_{LS}$ drives the combination of diode 200 and capacitor 201. This combination is the basic component of the peak detector. The principle of operation is very simple: the capacitor charges positively through the high forward conductance of the diode; the charge is prevented from leaking off through the diode because of its very high back resistance. Operational amplifier 203 must have a very high input impedance. Because any indeterminate length of memory is not desirable, resistor 202 discharges the capacitor slowly towards ground. The time constant of capacitor 201 and resistor 202 is approximately 10 seconds. The voltage gain of operational amplifier 203 is set to unity by the feedback resistors. The output of amplifier 203 passes over diode 204 to become "$V_{Peak\ Level}$". The most negative peak is similarly stored in a complementary circuit; this circuit is identical to the one just described except that the diode is reversed and the inputs to the operational amplifier are reversed. Output diodes 204 and 216 isolate the two halves of the circuit from each other; if the stored positive peak is 12 volts, while the stored negative peak is only 10 volts, the +12 voltage appears as $V_{Peak\ level}$. If the positive peak was only 10 volts, while the negative input peak was −12, a +12 volt level will appear on the $V_{Peak\ level}$ line.

RATIO CONVERTERS

Ratio converter 6 appears in detail on FIG. 2. It has two inputs: $V_{Peak\ Level}$ (from FIG. 3) and V average. The objective is to obtain the value peak V/Av V. This implies, of course, the mathmatical operation of division. Multiplication and division are two of the most difficult mathematical operations for a computer to perform, in either digital or analog form. Recently, however, a logarithmic amplifier has been developed in integrated circuit form, and this has greatly simplified the analog solution.

The mathematics are, briefly, as follows:
Since $$\text{Log } A/b = \text{Log } A - \text{Log } B$$

then $$A/B = \text{antilot } (\text{Log } A - \text{Log } B)$$

To accomplish the desired result, $V_{PL}$ is fed to the "A" input of logarithmic amplifier 125, while $V_{Av}$ is fed to the "B" input. For our purposes, the integrated circuit SN76502 consists of two independent logarithmic amplifiers, each having a pair of complementary outputs. At output Y, we therefore have $+\text{Log } V_{PL}$; at output $\overline{Y}$ we have minus Log $V_{PL}$. Similarly at output Z we have $+\text{Log } V_{Av}$; at output $\overline{Z}$ we have minus Log $V_{Av}$.

Two summing resistors 127 and 129 form the function Log $V_{PL}$−Log $V_{Av}$. At the same time, summing resistors 131 and 129 form the function Log $V_{Av}$−Log $V_{PL}$. These signals are presented to the complementary inputs of operational amplifier 140 whose output becomes a low impedance version of Log $V_{PL}$−Log $V_{Av}$.

It is now necessary to take the "antilog", and this is done by the circuits associated with operational amplifiers 150 and 155, and the single log amp 160. Basically, this circuit produces another log function, but it feeds back this log function negatively in such a way that the output of operational amplifier 150 is forced to become the antilog. Reference can be made to pages 7-40 thru 7-46, "The Linear and Interface Circuits Data Book" Texas Instruments, Inc. Dallas, Tex., or to any modern text on analog computation. The output of operational amplifier 150, therefore is the desired ratio of peak V/Av V.

SLOPE CONVERTER CIRCUIT 4

FIG. 3 shows the slope converter circuit 4 disclosed in the upper left corner of FIG. 1. Mathematically, its function is to *differentiate* the signal $V_{LS}$. This is accomplished physically by the use of the differentitating circuit composed of capacitor 250 and resistor 251. These have a time constant of approximately 0.1 second, which is in the range of major interest for the fibrillation detector instrument. The differentiated signal is relatively high impedance, and it is converted back to low impedance by operational amplifier 252, which is used with a unity voltage gain. The output of amplifier 252 represents the slope, or time rate of change, of $V_{LS}$.

PEAK SLOPE DETECTOR CIRCUIT 7

Also on FIG. 3 is shown the circuit for capturing the maximum value of the slope voltage. This circuit is identical to the circuit used for capturing the peak voltage level 2. The only difference is that one is capturing the peak voltage level and the other is capturing the peak of the slope voltage. The positive portion is processed by diode 253, capacitor 254, resistor 255, and operational amplifier 256. The negative peaks are processed by a similar but complementary circuit. The outputs are "OR gated" together by diodes 257 and 258 to become $V_{Peak\ Slope}$.

AVERAGE SLOPE DETECTOR

FIG. 3 shows a detailed circuit for average slope detector 8. This circuit is identical with average voltage level detector 3, shown in FIG. 2, except for input.

RATIO CONVERTER FOR PEAK SLOPE/Av SLOPE

This circuit is identical with that shown for the ratio detector of FIG. 2.

HEARTBEAT RATE DETECTOR 16

Figure 10:
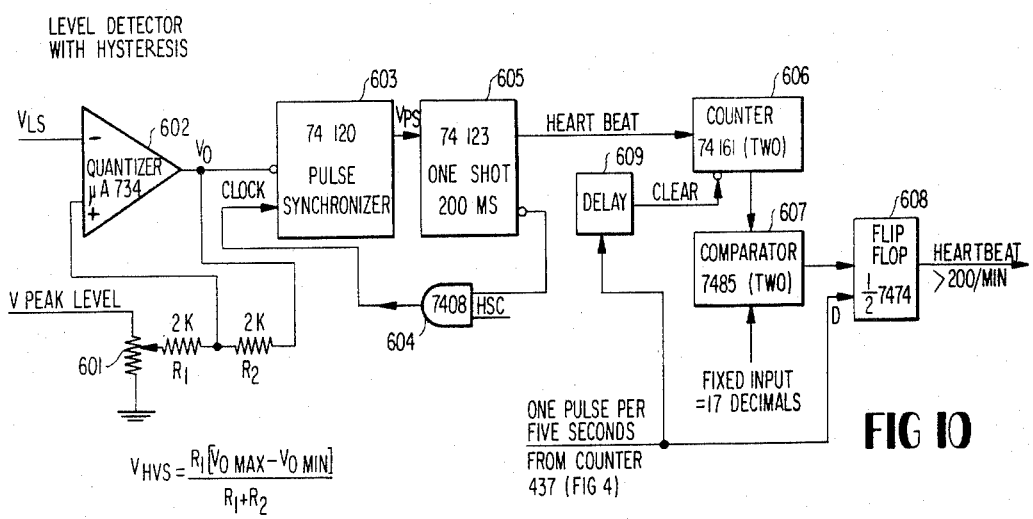
FIG. 10 illustrates in greater detail the heart rate detector 16 shown in FIG. 1.

The details of this circuit are shown in FIG. 10 "Heartbeat Greater than 200 Per Minute". The purpose of this circuit is to detect whether the rate exceeds 200 pulses per minute. If this condition occurs, the Defibrillator should be activated, even though the condition is not one of true fibrillation.

The two basic inputs to this circuit are $V_{LS}$ and $V_{Peak\ Level}$. Quantizer 602 recognizes each time that $V_{LS}$ dips below the peak level (modified by potentiometer 601). In order to prevent his circuit from making a series of outputs for only a single noisy crossing, hysteresis has been provided by the feedback resistors $R_1$ and $R_2$. The theory of this can be learned from any good analog textbook.

Pulse synchronizer 603 is "cocked" each time the input $S_1$ goes down following a previous high; the next clock "fires" the synchronizer, producing output $V_{PS}$. Because any re-occurrence of a true "R" pulse in less than 200 milliseconds is very unlikely, one-shot 605 together with AND GATE 604 prevent any clocks from occurring more often than 200 milliseconds. The positive output of One Shot 605 is called the heartbeat, and it is counted by counter 606. The counter output is continuously compared by comparator 607 to decimal 17. If, after 5 seconds the count is greater than 17, flip flop 608 is set; if not, the flip flop is cleared. Counter 606 is also cleared each five seconds, via delay 609. The output of flip flop 608 is called "Heartbeat Greater than 200 per Minute" and goes to the summer 13 via inverter 17 and diode 18.

REGULARITY DETECTOR

Figure 8:
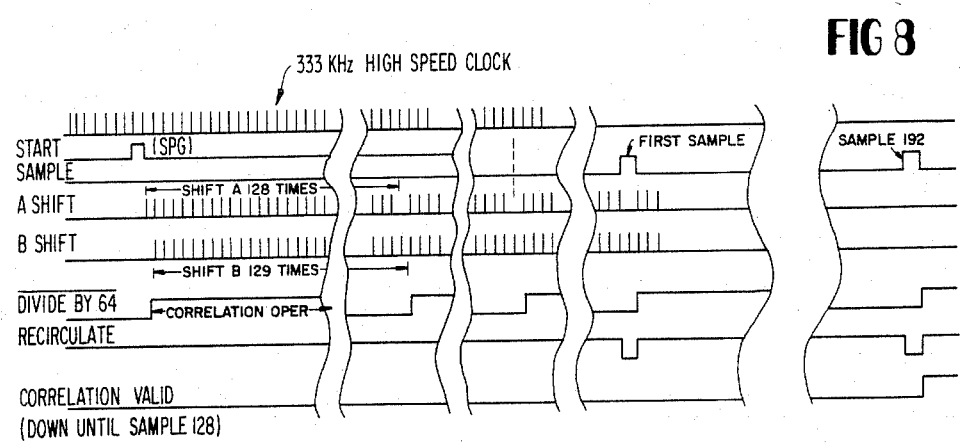
FIG. 8 is an electrical waveform chart illustrating the timing of the various electrical circuits.

FIG. 4 shows the details of regularity detector 5. The waveforms associated with it are shown in FIG. 8.

There are many ways to measure the similarity of a pattern to another. One of the methods is to produce a Fourier analysis and observe to what degree the coefficients remain stable over some length of time. The hardware required to do this in "real time" is fairly formidable, however, and more direct digital autocorrelation method will be illustrated herein, instead.

Basically, the method is to store two different time sections of the waveform and compare them point by point; since the relative "phase" of the recurring pattern of the two sections is unknown (assuming the waveform is repetitive) every possible phase is tried. The best value of correlation for these two times sections is stored; two more time sections are then selected and correlated in the same manner. This operates continuously, and the best value of correlation occurring since the beginning is stored and continuously presented.

The salient components of FIG. 4 are the input zero crossing detector 400 (which produces a positive output if the input waveform is positive, and a negative output for a negative input; these are digital outputs), the "A" shift register 404, the "B" shift register 413, the serial correlator 420, and the group of circuits 422, 423 and 424 which add up the points of similarity and retain the best score.

Note that the A register is 64 bits long, while the B register is 128. The reason for this will be explained in a later paragraph.

The circuits of FIG. 4 will now be discussed at an intermediate level of detail. Samples are taken from the signal line $V_{LS}$ at a rate of 40 per second (i.e., every 25 milliseconds). Each sample is accompanied by a shift in both the A and B registers. As far as loading data is concerned, the A and B registers can be considered to be a single register of 192 bits capacity; thus, it takes 192 shifts (at 40 per second) before these registers are fully loaded. When both registers are finally loaded, correlation of the two sections can begin. This is accomplished by shifting both registers at a much higher speed, 330 KHz. The bits from the ends of the two registers are compared by exclusive or gate 420; this circuit produces a "zero" output when the two inputs are both "ones"; it produces a "zero" output also when the two inputs are both "zeroes". The other two cases produce a "one" output. This pulse train is inverted by inverter 421 and the number of "ones" is counted by the new value counter 422. At the end of 64 of these correlation shifts, the binary output (called new value) is compared to the binary output of the best value register 424. This comparison is done by comparator 423. If the new value is larger than the best value, the new value is substituted for the old number in the best value register. Following this, the new value register is cleared.

During the correlation operation, each register has been recirculating back on itself, thus saving the data. 128 shifts have to be provided to get both registers back in the proper relationship. At the end of these 128 shifts, a "special shift" is supplied to the B register, such that the phase of its contents is now advanced one sample position ahead of the A register. Another correlation operation consisting of 64 high speed shifts is now activated. The number of "ones" resulting from this operation is counted by the new value counter 422, and the result, after 64 shifts, is compared to the output of the best value; otherwise the best value register retains its previous value. Note that 64 more shifts must be made to get the two registers back in their same relative position as they had before beginning the correlation operation.

These correlation operations, with their special shifts to the B register, continue for 64 times. At this time a new sample is taken and entered into the A register; concurrently a bit is taken from the end of the A register and supplied to the input of the B register. The extra bit at the end of the B register is not recirculated but is simply dropped off, its usefulness now being at an end. The best value register is cleared at this time, (each sample time). Another complete set of 64 correlation operations are again performed, with best values being stored in the best value register. As will be explained later, the best value register is kept clear during the first 192 samples, since no valid correlations can be obtained until both the A and B registers are full.

The sequence continues indefinitely as long as the power is on. The output value of the best value register is continuously driving a digital-to-analog-converter 425; thus, the "regularity" output is continuously available following the first 192 samples (4.8 seconds are required for this initial loading).

The reason that the B register is twice as long as the A register is that the information in the B register is "slid" with respect to the A register. Since 64 points are correlated at each one of 64 phases, it is necessary that the B register contain a full 128 points sampled from the continuous input signal.

The operation required in produceing the regularity circuit can be explained in more detail by referring to FIG. 8, "Timing for Regularity Detector" in conjunction with the control circuits shown in the lower part of FIG. 4. A high speed clock 430 is running all the time the power is present. Its frequency is approximately 330 KHz. When start switch 435 is depressed, the start pulse generator 436 produces a single pulse. This stage has two complementary outputs SPG and $\overline{SPG}$; between the two of them, all stages requiring clearance are cleared at this time. As explained previously, it is necessary to load 192 samples into the registers before valid correlation can begin. These samples are generated by a series of clock dividing circuits. The first one of these is counter 431, which produces an output called divide by 64, and another output called divide by 128. The latter output triggers a one shot multivibrator 432 which generates a special shift window. This pulse train is, in turn, divided by 64 by counter 433; the output of counter 433 produces a pulse 40 times a second which is used to produce the sample. The sample pulse train is divided by 192 in counter 437; when this count is completed the first time, correlation valid flip flop 438 is set and remains set until the next time that the start switch is depressed.

Although no correlations are valid until flip flop 438 is set, all the shifting waveforms shown in FIG. 8 are operating from the time that power is first turned on. As explained before, the correlation operation period consists of 64 shifts; 64 more shifts, plus a special shift for the B register, are required before the next correlation operation period occurs. The correlation operation period is identical to the signal $\overline{\text{Divide-by-64}}$, shown in FIG. 8.

The only difference between the A shift and the B shift is that the B shift has an extra pulse, called the special shift. This is produced in the following way: high speed clock 430 runs continuously and is counted by counter 431. When the divide by 128 output goes up, it triggers one-shot multivibrator 432. This is an asynchronous pulse (SSW) just wide enough to overlap the next clock pulse; its output goes through NOR gate 440 and keeps counter 431 clear, instead of letting it make another count on the overlapped clock pulse. The A shift is produced by AND gating the high speed clock (HSC) with the complement of SSW in AND gate 405. The result is 128 shifts followed by a one clock width gap, for the A shift. The B shift is simply the high speed clock itself, through buffer 414.

Note that sample and recirculate are merely complements of each other. Each time that a sample is required, the recirculation paths of the shift registers are broken and a new bit of data inserted.

ENHANCED REGULARITY DETECTOR

It a more sensitive regularity detector is needed (one which produces a larger distinction between patterns having a fair degree of regularity) an excellent way to accomplish this is by using more of the amplitude information of the data. A four level system (instead of the two level system just described) requires that the zero crossing detector 400 be replaced by a 4 level quantizer which produces a two bit output for each sample. This stage can be called a two bit analog to digital converter. These two bits can be stored in either a parallel or serial representation; twice as much shift register storage is required as for the two level system. Such enhancement of the circuit shown in FIG. 4 to produce higher sensitivity autocorrelation performance is easily accomplished by one skilled in the art.

DESCRIPTION OF THE SUMMER CIRCUIT

Figure 9:
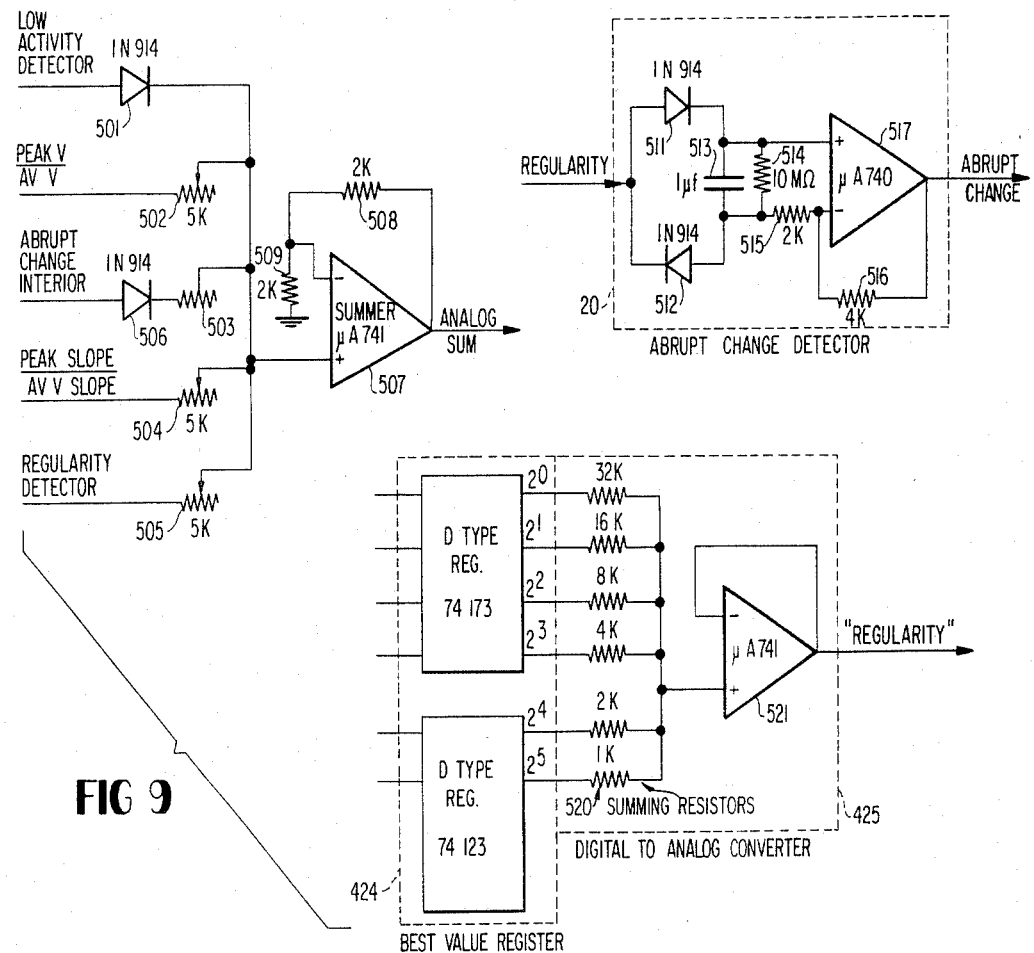
FIG. 9 is a circuit illustrating the summer circuit 13 and digital to analog converter of FIG. 1.

FIG. 9 shows the details of the summer circuit. Three of the inputs to this circuit are summed by using variable resistances 502, 504, 505 and whose maximum value is 5 kilohms. These are the peak V/Av V, the peak slope/Av slope, and the regularity. The abrupt change detector is summed via diode 506 and variable resitor 503. The reason for the diode is that when the abrupt change output is low, this does not indicate a fibrillation condition. When it is high, however, it indicates the probability that ventricular tachycardia is occuring, which is not to be treated by shock. Likewise, a low voltage output from the low activity detector does not indicate fibrillation, but a high voltage output does indicate that the condition is not to be treated by shock. The summing path contains diode 501 but does not include a variable resistor, since the low activity detector puts out strictly binary information.

The reason for using variable resistors instead of fixed resistors is to allow their relative weights to be determined by experience.

The voltage applied to the summing element inputs, and the relative values of the summing resistors, develop a voltage determined by Ohm's Law. This voltage is merely buffered by operational amplifier 507; its gain is determined by feedback resistors 508 and 509, which are set for approximately unity gain.

DESCRIPTION OF THE ABRUPT CHANGE DETECTOR

FIG. 9 also shows details of the abrupt change detector 20. The analog output of the regularity circuit (FIG. 4) is the input to this circuit. In electronic terms, this is simply a "peak-to-peak" measuring device. The greater the difference between the most positive peak of the input and the most negative peak, the more positive will the output be. In other words, the more the ECG pattern changes, the more positive the output.

Diodes 511 and 512 charge capacitor 513. The capacitor, together with resistor 514, provides a ten second time constant. The operational amplifier 514 amplifies the difference between the two inputs of approximately two. This gain is set by the value of resistors 516 and 515.

DESCRIPTION OF THE DIGITAL TO ANALOG CONVERTER

FIG. 9 also shows the details of digital to analog converter 425. The outputs of the best value register 424 form the input signals to the D/A converter. The outputs of the 74173 integrated circuits are single ended and go positive when a "one"0 is represented. They can "pull up" a resistor when they are high and they can "pull down" a resistor when they are at ground. Assuming the two output levels of the register are zero and +4 volts, the output of the resistor network is zero volts for a count of zero, and +4 volts for a count of 63. If there is a count of one in the register, the $2^0$ output will be at +4 volts, while all the rest are at zero volts. Thus, there will be 32K pulling up and 32K/62 pulling down, producing an output voltage equal to $(1/63) \times (4$ volts), or 0.063 volts. Although the circuit shown is not highly accurate, it is quite sufficiently accurate for the application.

Low impedance output is provided by operational amplifier 521, used in the unity voltage gain configuration.

SYSTEM BLOCK DIAGRAM

FIG. 11a shows the system block diagram. It is basically composed of electrocardiograph 702, fibrillation recognition circuitry 703, and the defibrillator 704.

Input paddles 701 are attached to the patient. There may be either two or three of these paddles. Although the normal output of an ECG machine is a strip chart with voltage as a function of time, this system does not use the hard copy output except as a record. Instead, the electrical output of the ECG is used; this is the signal which drives the galvanometer of the strip recorder. The electrical output signal drives the fibrillation recognition circuitry 703.

There are several connections between the fibrillation recognition circuitry and the defibrillator 704. The transer pulse activates the shock; the line SOS activates a change in the amount of energy per each shock. This latter function is provided by stepping switch 704, which provides three different values of total energy delivered to the patient. These are typically 100 joules, 200 joules, and 400 joules. Before each shock, the stepping switch is advanced one step, so that the next shock, if necessary, is delivered at an increased level. The output paddles 705 are connected to the patient.

FIG. 11b shows in more detail the controls (located inside the fibrillation recognition circuitry 703) which govern the transfer pulse and the stepping pulse SOS. When the equipment is first turned on and activated, the start pulse SPG resets the stepping switch 706 (FIG. 11a) to the zero charge position. Note that there are four step points in the switch. SPG also clears transfer flip flop 712 via NOR GATE 711.

If the line ventricular fibrillation occuring is up at the time the pulse per 5 seconds comes up, AND GATE 710 will give an output, turning on step one shot 714. This lasts for 100 milliseconds and advances stepping switch 706 to the 100 joule position. The transfer flip flop 712 is turned on by the trailing edge of SOS. The transfer flip flop stays on until the next time that the one pulse per 5 seconds comes up. It is then cleared. If, at that time, fibrillation is still occuring, then AND GATE 710 becomes true again, SOS advances the stepping switch, and the transfer flip flow is again turned on; this time a 200 joule shock is produced. Another similar sequence will produce a shock of 400 joules. Due to the design of stepping switch 706, additional stepping pulses produce no motion of the switch, and the system will continue producing 400 joule pulses until deactivated.

The paddles may be three-lead circuited, such as those manufactured by Physio Control. The contact surfaces of the paddles are coatedly evenly with a conductive jel, and are then positioned on the patient's bare chest in the normal locations—one near the sternum and the other to the left of the left breast. The paddles may be held in place by hand or by a harness or strap (not shown). This harness or strap serves another purpose in that its fastening fixtures are calibrated in accordance with its length. Hence, when it is fastened to the patient, it automatically determines the size of the patient and so the intensity of the shock to be administered. With the paddles in place, the machine is switched on. The fibrillation detector 703 circuit is engaged and it picks up the impulse wave from the heart. The ECG waveform is analized through the fibrillation detector 703 described earlier which identifies the desired pattern types. The tell tale functions of the waveform are determined and compared to the parameters established in the circuit shown in FIG. 1. Should the waveform be coincident with the parameters, set forth about (e.g. the absence of a known feature) the circuit is switched off and the defibrillator 704 circuit is engaged. This is the circuit which delivers the shock. The defibrillator is a commercially available unit and from the time the unit is switched on, the shock unit, a standard capacitor is being charged. Even though the capacitor is always fully charged, the intensity of the current delivered to the paddles has been predetermined by the adjustment setting of the holding harness. This establishes the minimum, or first shock, the step-ups if any, and the maximum shock as predicated on the weight of the patient. These intensities are accomplished through a series of resistors which are latched in or out of the circuit to assure that the proper charge is delivered to the paddles. Immediately following discharge, the defibrillator circuit 704 automatically cuts off, the capacitor begins to recharge, and a time delay of preset duration sets in to provide time for the effect of the shock to be evaluated. The fibrillation detector circuit 703 is again automatically engaged and another "reading" is taken on the waveform. If the waveform indicates continuing fibrillation, the defibrillator 704 circuit replaces the fibrillation detection circuit automatically and the charge delivered to the paddles is increased to the next increment. This entire process will automatically repeat until the maximum charge is reached and activated, or until the waveform indicates fibrillation has ceased and a more normal condition exists. With this "normal" condition, the secondary circuit cuts out, any charge in the capacitor is safely discharged internally in the machine. With the waveform indicating a stabilized condition, a low output current of approximately 0.5 joules takes over at a preset rate, acting as an external pacer to maintain the stabilized condition.

An oscilloscope, not shown, may be built into the unit and the paddle's circuitry to visually inform the operator of the patient's continuing condition.

It should be noted that adequate safeguards are built into the unit to protect the safety of the patient at all times. In the event of any malfunction, the charge is automatically discharged internally in the machine. Treatment is begun at a relatively low intensity and is increased in increments as needed so that the patient is at no time exposed to an excessive charge which could result in burning or in heart damage.

In summary, the invention performs three functions:

(1) It determines if the heart is in ventricular fibrillation.

(2) If positive, if automatically administers a proven method of treatment to stabilize the heart function without any risk of exposure to excessively high shock intensity.

(3) After the condition is stabilized, it takes over as an external pacer to maintain the stabilized condition until the patient can receive proper medical treatment.

While there has been shown and described a preferred embodiment of the invention, it will be appreciated that the invention is capable of various modifications and adaptations which whould be obvious to those skilled in the art and come within the spirit and scope of the invention as defined in the appended claims.

What is claimed is:

1. Ventricular fibrillation detector comprising, electrode means for application to a patient's chest,
   means coupled to said electrodes for producing an electrocardioggram waveform of the patient's heart,
   electrical circuit means forming a library of features of known electrocardiogram waveform characteristics of various heart conditions,
   electrical circuit means for comparing the electrocardiogram waveform of said patient against said library of features of known known electrocardiogram waveform characteristic of various heart conditions, and
   indicator means for indicating the absence of all of said stored characteristics in said electrocardiogram of the patient's heart as ventricular fibrillation.

2. The invention defined in claim 1 including defibrillator means coupled to said electrode means, and means for activating said defibrillator means upon said indicator means indicating the absence of any of said stored characteristics in the patient's electrocardiogram waveform.

3. An automatic defibrillator comprising,
   electrode means for application to a patient's chest,
   means for storing a plurality of known electrocardiogram waveform characteristics of various heart conditions,
   means coupled to said electrodes for producing an electrocardiogram waveform of the patient's heart,
   electrical circuit means for comparing the electrocardiogram waveform of said patient against each stored characteristic,
   circuit means electrically coupled to said means for comparing for determining the absence of all stored electrocardiogram waveform characteristics of various heart conditions in the electrocardiogram of said patient,
   defibrillator means electrically coupled to said electrodes, and
   means for causing said defibrillator means to apply defibrillating electrical energy to said patient via said electrodes upon said circuit means detecting the absence of all stored electrocardiogram waveform characteristics of various heart conditions in said patient's electrocardiogram.

4. An automatic defibrillator apparatus as defined in claim 1 including means for successively increasing the shock energy applied to said patient from a predetermined level to a predetermined maximum level until ventricular fibrillation is terminated.

5. An automatic defibrillator as defined in claim 3 including means for detecting the cessation of ventricular fibrillation and the onset of a stable condition in said patient and producing a signal corresponding thereto, and switch means controlled by said signal upon cessation of ventricular fibrillation and the onset of a stable condition for applying a low current to said electrodes to pace the patient's heart.

6. The automatic defibrillator defined in claim 5 wherein said low current has an energy value of about 0.5 joules.

7. An automatic defibrillator as defined in claim 3 wherein said known electrocardiogram waveform characteristics of various heart conditions include:
   (1) peak amplitude values which are large compared to the average amplitude values of the patient electrocardiogram waveform,
   (2) peak slopes the patient's electrocardiogram waveform which are large compared to average slopes, and
   (3) substantially uniform periods of repetition in said patient electrocardiogram waveform.

8. An automatic defibrillator apparatus as defined in claim 7 including means for producing signal voltages corresponding to said waveform characteristics (1), (2), and (3), and a summer electrical circuit for summing the said signal voltages corresponding to the peak amplitude, the peak slopes and uniformity of repetition rate controling said defibrillator means in accordance with the output from said summer circuit.

9. An automatic defibrillator as defined in claim 8 including means for detecting an abrupt change in the repetition rate of said waveform characteristics, and means for inhibiting the operation of said defibrillator when an abrupt change is detected in said rate.

10. An automatic defibrillator as defined in claim 9 including means for detecting the heart beat rate of said patient in said electrocardiogram waveform of the patient's heart and producing a further signal supplied to said summer circuit.

11. An automatic defibrillator as defined in claim 10 including means connected to said circuit for detecting the peak amplitude levels of said electrocardiogram waveform of the patient's heart, means for comparing said peak level amplitude with a reference amplitude value and producing a low activity signal which is applied to said summer circuit.

12. A method of treating ventricular fibrillation in a patient, comprising,
   storing a plurality of electrocardiogram waveform characteristics of various heart conditions,
   applying electrodes to said patient and producing an electrocardiogram waveform,
   comparing the electrocardiogram waveform of the patient against each stored characteristic to detect the absence of all stored electrocardiogram waveform characteristics of various heart conditions in the patient's electrocardiogram and,
   only upon detecting the absence of all of said stored characteristics, administering corrective electrical impulses to said patient's heart.

13. The method of treating ventricular fibrillation defined in claim 12 including means operative upon cessation of ventricular fibrillation and the onset of a stable condition for applying a low current to the electrodes to pace the patient's heart.

* * * * *